United States Patent
Hoff et al.

(10) Patent No.: US 7,379,530 B2
(45) Date of Patent: May 27, 2008

(54) METHOD AND APPARATUS FOR THE SAFE AND RAPID DETECTION OF NUCLEAR DEVICES WITHIN CONTAINERS

(75) Inventors: Paul W. Hoff, Bedford, NH (US); Stephen R. Blatt, Bedford, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 0 days.

(21) Appl. No.: 11/477,966

(22) Filed: Jun. 29, 2006

(65) Prior Publication Data

US 2007/0237294 A1 Oct. 11, 2007

Related U.S. Application Data

(60) Provisional application No. 60/789,750, filed on Apr. 6, 2006.

(51) Int. Cl.
*G01N 23/04* (2006.01)
(52) U.S. Cl. .......................... 378/57; 378/108
(58) Field of Classification Search ................ 378/57, 378/108, 146
See application file for complete search history.

(56) References Cited

U.S. PATENT DOCUMENTS

| | | | |
|---|---|---|---|
| 5,703,923 A * | 12/1997 | Bardash ...................... | 378/87 |
| 6,088,423 A * | 7/2000 | Krug et al. .................. | 378/57 |
| 6,507,025 B1 | 1/2003 | Verbinski et al. | |
| 6,552,346 B2 | 4/2003 | Verbinski et al. | |
| 2006/0193434 A1* | 8/2006 | Green ......................... | 378/57 |
| 2006/0256914 A1* | 11/2006 | Might et al. ................. | 378/57 |
| 2007/0025505 A1* | 2/2007 | Bjorkholm .................. | 378/53 |

\* cited by examiner

*Primary Examiner*—Hoon Song
(74) *Attorney, Agent, or Firm*—Robert K. Tendler; Daniel J. Long

(57) ABSTRACT

A safe, reliable and rapid system for the detection of nuclear materials within containers includes the use of pulsed high-intensity gamma rays that can penetrate a container and its contents and can be detected outside the container to provide a display in which high-Z material, including lead, uranium, plutonium and other nuclear substances that absorb gamma rays are detected as black regions on the display. In one embodiment, orthogonal pulsed gamma ray beams illuminate the container from two different directions to provide three-dimensional slices from which the existence and location of nuclear threat materials can be ascertained in as little as four seconds for a 40-foot container.

19 Claims, 5 Drawing Sheets

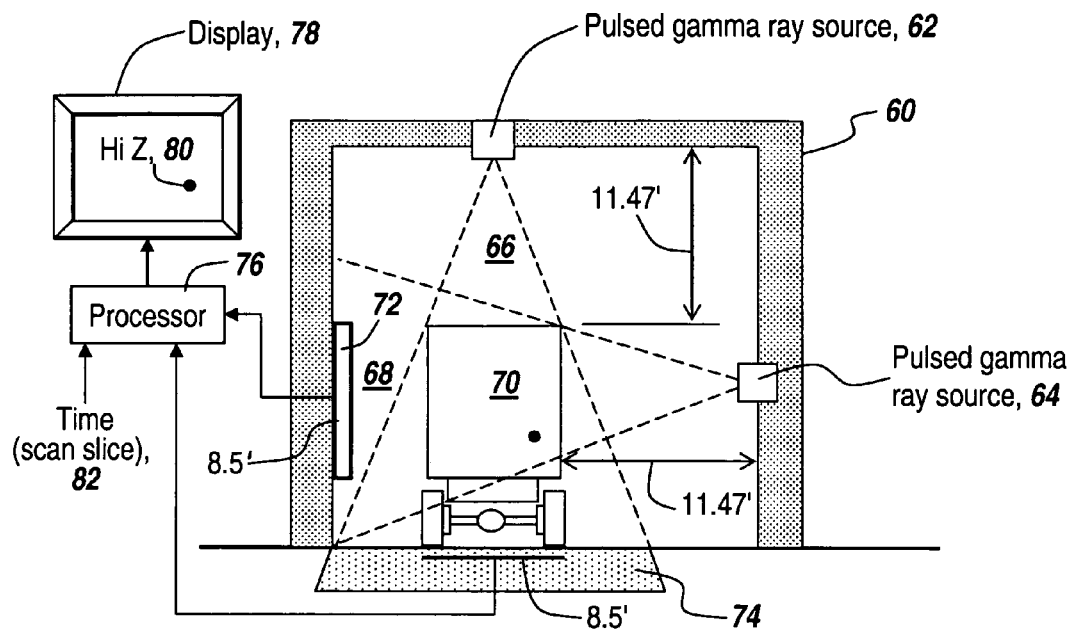
Fig. 6
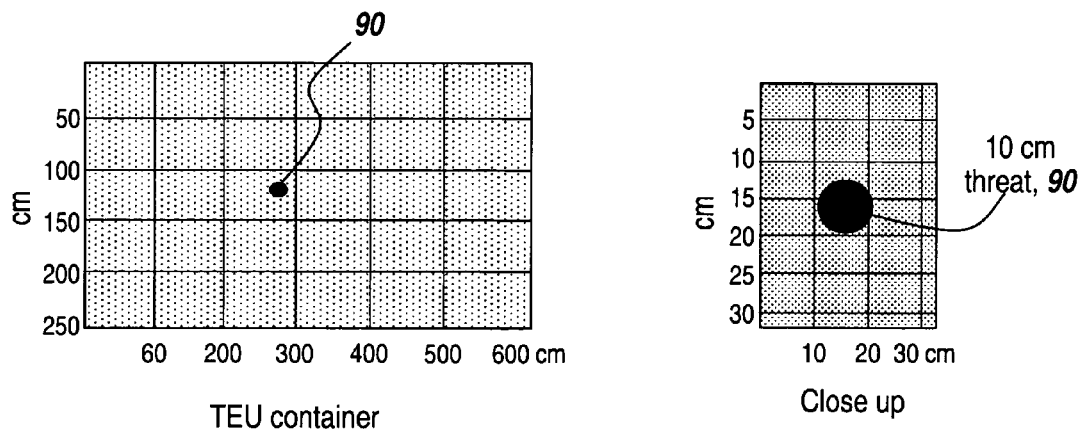
Fig. 7
Fig. 8

1 TEU container with 10 cm
threat replacing one of 226 engine blocks

METHOD AND APPARATUS FOR THE SAFE AND RAPID DETECTION OF NUCLEAR DEVICES WITHIN CONTAINERS

RELATED APPLICATIONS

This Application claims rights under 35 USC § 119(e) from U.S. Application Ser. No. 60/789,750 filed Apr. 6, 2006, the contents of which are incorporated herein by reference.

FIELD OF THE INVENTION

This invention relates to cargo screening and imaging and more particularly to a high-speed system for container inspection that is both exceedingly accurate and safe.

BACKGROUND OF THE INVENTION

As is well known, nuclear materials can be smuggled into the United States by being hidden in cargo containers or vessels. Scanners have been developed that image cargo containers utilizing gamma rays. However, these scanners use low-intensity continuous gamma rays that are not powerful enough to pass through fully loaded cargo containers to detect nuclear materials hidden in the cargo.

Nuclear materials can be smuggled into the country amongst, for instance, frozen food, such as fish, in which the water within the food acts as a moderator to the radiation from any nuclear materials embedded in the food.

Moreover, nuclear materials can be hidden in lead containers such that passive techniques such as Geiger counters cannot be utilized to detect the presence of nuclear materials. Containers can be 40-foot trailers or smaller containers that go into aircraft, small ships or even fishing boats.

More particularly, in the past shipping containers that may be from 20 to 40 feet in length have been subjected to a passive screening system involving Geiger counter-type detection. In these systems, the Geiger counter is passed adjacent the containers looking for radioactive materials.

This system can be easily defeated because one can take the materials and put them inside a lead container such that radiation does not pass out of the container. One could also place the materials inside a large amount of water. One could therefore place the nuclear material adjacent a shipment of bottled water and utilize the bottled water as a shielding agent so that the nuclear material cannot be passively detected.

As a result, active screening approaches have been utilized that illuminate the cargo container, most usually made of steel, and to do so utilizing a technique that can see through the steel and see through most of the container contents. These types of systems include gamma ray sources, with the gamma rays being utilized for illumination.

Those systems that utilize gamma rays in general use continuous sources of gamma rays, with the sources not having a very high intensity. These sources thus are characterized by low brightness. The result of utilizing these sources is that the system cannot see through large amounts of cargo.

Thus if one has a container full of frozen fish, to the extent that the containers are full, this is equivalent to having a container full of water. As is well known, fish are 70% water and the gamma rays become absorbed so that they do not make it all the way through from one side of the container to the other.

These systems operate on the principle that one has a source on one side of the container and a detector on the other side of the container. If the container is filled with water or gamma-absorbing material, one does not get sufficient signal at the detector to be able to reliably ascertain what is in the container.

Similarly, if a container has cargo involving a large amount of metal, such as associated with moving machine parts, one needs to use very high-intensity gamma rays to penetrate from the source through the container to the detector.

It is noted that radioisotope sources are continuous sources because the gamma rays are emitted continuously, with the gamma intensity depending on the exponential decay of the radioisotope. These sources are not very bright unless one has a large amount of radioactive material. However, if one utilizes a large amount of radioisotope material, this presents its own threat. Moreover, if a terrorist wished to cause damage, he could, for instance, blow up the detector system itself to generate a cloud of radioactive material that could drift into populated areas.

Moreover, the use of large quantities of radioisotopes poses a threat to people who are working around the port or the docks, including customs officials that have to go by the radioactive source every day. Thus the radioactive source emits continuously and must be shielded and protected against terrorist attack.

These sources are usually contained in lead having an aperture that is controllable such that radiation comes out of the lead shielding only when the aperture is opened up to irradiate the container and then only in the direction associated with the aperture.

In practice one has a container placed on a truck bed, such that when the container is offloaded from the ship to the truck, it is then driven up to the radioactive detector. The truck stops and the driver gets out, after which the truck is moved through the scanner having this continuous radioactive source such that the container is passed by the source. The container passing by the source can also result in scattering off of the material in the container, again providing a health hazard.

Most importantly, with such continuous low-level sources to be effective at all, the scanning time for a 40-foot container is on the order of minutes. In a busy port facility, the speed at which the containers can be scanned in this manner limits the number of containers that can be scanned to something considerably less than 100% of all of the available containers.

There are other types of systems in which neutron particle streams penetrate material that is housed in the container, at which point one looks for fluorescence that is emitted as a result of bombardment with neutrons. For high-Z materials, having atomic weights equal to lead or higher, for instance uranium, one obtains characteristic signatures out from the irradiated material because as the neutrons come in and strike the nuclei, the nuclei relax and emit radiation in the form of fluorescence. However, this type of system is exceedingly slow in terms of scanning, mainly because of the low intensity of the neutron stream due to the small number of neutrons that can be obtained from the neutron source.

In most neutron-type scanning systems, the system utilizes a particle accelerator that accelerates particles that when broken apart produce neutrons.

One problem with such a system is that neutrons going through the contents of a container can damage the contents. In one sense, neutrons are more damaging than gamma rays.

Also the provision of a particle accelerator is impractical because of the large investment necessary for each scanning station. Most importantly, neutron beams present a safety hazard. This means that it is unsafe for personnel near the area. One therefore has to clear the area before the neutrons are emitted.

Moreover, the neutron source is again a low brightness source that requires a long scan time.

The systems that utilize a neutron beam sees high-Z material because as the neutrons hit the high-Z material, they get absorbed. This is true both for lead, and other high-Z materials such as uranium or plutonium.

Also the neutrons impinging upon various nuclei may cause fluorescence so that one obtains a signature characteristic of the embedded nuclear material, which is different from the signature that one might obtain from the cargo itself.

Note also, with respect to the neutron beam systems, one has to be able to accommodate various different types of containers and various different types of cargo, each of which can absorb the neutrons and cause the fluorescence. Thus the generation of a signature must take into account the various absorbing material between the source and the detector. Depending on the type of contents of the container, one might not be able to properly read the signature to determine the presence of high-Z material within the container.

In addition to the systems utilizing radiologic sources, there is yet another type of system that utilizes a LINAC, which is an accelerator to create gamma rays as opposed to using a radiologic source. LINAC-induced gamma rays are, however, of low intensity and likewise is a continuous source of gamma rays.

One therefore obtains a relatively low intensity over a number of seconds such that the average intensity that irradiates the cargo and comes out the other side is quite low. If one has low brightness in any given millisecond or nanosecond interval, then the detected result may be in the noise level.

Note that requirement is to be able to scan the container as quickly as possible and as safely as possible, with the accuracy in determining the presence of high-Z material being paramount.

SUMMARY OF INVENTION

Rather than utilizing continuous low-level gamma ray sources, be they radiological or produced by a LINAC, and rather than utilizing either passive gamma ray detectors or neutron beam scanning devices, in the subject invention one utilizes an extremely bright source that emits pulses of gamma rays over short periods of time. In one embodiment the pulsed gamma ray source provides gamma ray pulses on the order of picoseconds. This results in a much faster scanning time than has heretofore been possible.

In one embodiment, the pulsed gamma source and the detector array can scan a 40-foot container driven or conveyed through the detector at 15 miles an hour, which is the usual speed at which trucks move throughout the port; and be able to accurately detect nuclear threats within four seconds as opposed to minutes.

The speed at which the scanning can occur can be seen in terms of characterizing the scanning as a strobe source versus a daguerreotype system and by comparing daguerreo-type speeds with stroboscopic speed.

The high-intensity pulsed gamma source enables non-intrusive inspection of every container, with inspection speeds increased by an order or magnitude over those associated with prior systems. In one embodiment one can inspect 900 40-foot containers per hour versus the Cargo Advanced Automated Radiography Systems (CAARS) goal of 120 per hour.

The subject system enables the detection and location of nuclear material by providing the location of high-Z materials within the container. Note, upon detection of high-Z materials, the container load can be further screened using other, slower techniques. The key attributes of the subject system are accuracy, safety and speed.

Note that the high intensity of the subject sources allows multiple views of each slice of the container while it is on the move, all the while minimizing radiation exposure to levels comparable to dental X-rays. The result is that even for potential stowaways in a container, the scanning with the subject system is far from lethal.

Note also that the throughput for the subject system is such that one can scan each and every individual shipping container that comes off a ship, with the subject system being scaleable to both larger and smaller applications, from 300 gross ton ships to aircraft cargo containers.

It will be appreciated that the use of a high-intensity pulsed gamma source provides 100% screening of containers and the identification of those containers requiring further inspection.

Note that port operators have identified increased labor cost as the key obstacle to the implementation of 100% non-intrusive inspection. Scanning containers moving at the typical shipyard speed of 15 miles per hour minimizes the amount of time and labor spent in container inspection.

In one embodiment the containers are driven through a "drive-through" portal stationed to conduct real-time high-speed screening of all containers.

In the portal in one embodiment there are two pulsed gamma sources and two detector arrays along orthogonal axes. The system is arranged to produce a 3D image that indicates both the presence and high-resolution location of high-Z material that might be shielding nuclear materials within the container.

Upon such an alert, the screening operator can accurately cue a subsequent, lower-speed inspection system for suspected containers.

As mentioned above, an active high-intensity source is needed to penetrate fully loaded containers. Using a high-intensity pulsed gamma source allows one to distinguish high-Z material from routine cargo. Since the source is a sufficiently bright gamma source, the signal processing required to detect targets can be minimized.

A nuclear threat will be detected as an appropriately sized black object compared to other objects in the container that, because they are more easily penetrated by the gamma radiation, will show up at lower contrast than the target. The probability of false alarm due to misrepresentation of the scanner output is minimal, since resolution in one embodiment is ½ inch.

Moreover, with a pulsed high-intensity gamma source, inspection speeds can be increased by an order of magnitude over the stretch-goal inspection speed of CAARS.

In one embodiment, low-cost detector arrays use bulk CdZnTe detectors grown utilizing the horizontal Bridgeman technique, rather than NaI(Tl) scintillation detectors.

Because of the high-intensity gamma source, the CdZnTe detectors can be used as bulk detectors, with voltage gated for the gamma pulses. The above attributes allow a much lower cost than the current spectroscopic use of CdZnTe.

The pulsed gamma ray sources produce intensities of $5\times10^{11}$ gammas in $10^{-18}$ seconds, with a projected spectrum of 1-3 MeV.

In one operative embodiment, one obtains two photons in each ½-inch detector element for the following lengths of materials: iron: 12 inches, scaleable to greater than 16 inches; and water: 135 cm. The output image of a maximally loaded container of water involving frozen fish provides for an easily detectable threat.

Moreover, for instance in a shipment of automobile engines, if one engine is removed from a full load of automobile engines and replaced with nuclear material, it will nonetheless be easily detectable. The detection involves the existence of dark spots in the detected image that show the high-Z materials that might be shielding the nuclear materials.

With the pulsed gamma source, the radiation level in the container is approximately 0.1 mrem. This means that a stowaway in the cargo container will receive a dose approximately equal to $\frac{1}{20}^{th}$ of a dental X-ray. Moreover, the driver will be shielded from direct exposure by a gating system, with indirect dosing caused by scattering being no more than 0.001 mrem.

As noted above, the subject system will detect all high-Z materials from lead on up and beyond, including uranium and plutonium, meaning any substance that has an atomic mass equivalent to or higher than lead.

Moreover, in the case of a shipment of batteries, one can ascertain that there are a number of lead batteries because of the massive number of dark areas that are contained within the display. If this occurs, one singles the shipment out for special inspection.

The pulsed gamma source used is $10^4$ brighter than any of the continuous sources, which makes the detection of nuclear materials possible.

Thus, while it may take a minute or more to scan a container by moving the container through a continuous radiologic source, the subject system can scan the same container in four seconds.

Moreover, as to the ambient radiation, the radiation from a radiological source which because it is continuous and exists over a long period of time relative to the subject system results in more photons irradiating individuals.

For single container inspection at foreign ports it is noted that the subject system can be used in the vicinity of ships and cranes generally located in a secure area. The toll booth-type inspection system minimizes economic impact because there is no slow-down for inspection.

Each container is inspected just prior to loading in a vetted ship. This supports the "24-hour rule." Moreover, if a threat is detected, the particular container is pulled off for manual inspection. The use of the high-brightness source with good contrast ratios provides a simple go-no go decision for manual inspection.

Moreover, the images can be viewed in port and, if desired, in the United States.

It is noted that the ultra-short pulsed gamma source does not use radiologic material, with the gamma rays being sufficiently intense to create an image of the container such that high-Z materials that absorb gamma rays show up as recognizable dark spots. Since the container can be probed in two directions with multiple sources one can accurately locate a threat and minimize false alarms.

In short, no radioactive material is needed to produce the gamma rays and the ultra-short pulsed gamma rays can be generated on demand only when the container is inside the scanner volume.

The pulsing gives high peak intensity to the gamma rays, yielding greater contrast ratios with much less exposure. The system also permits fine resolution and high throughput, with the detector array size chosen to give multiple exposures to each container slice as the truck moves through the scanner.

What is provided is a robust detection system that is able to see through fully loaded containers and at the same time produce images that can be easily detected by an automated alert program.

In one embodiment, each single TEU container is scanned to a ½-inch 3D resolution in less than 2 seconds, with each detection area pulsed four times, two pulses horizontally and two pulses vertically, for a combined scan time of 4 seconds.

In this embodiment, the contrast ratio between cargo, steel or water, versus target material is greater than $2\times10^2$.

Each detector element has a signal-to-noise ratio greater than $10^5$ over the background and has greater than $2.0\times10^6$ visible protons created in each scintillator element, thus to permit inexpensive solid-state detectors.

As to potential effects on humans, there is minimal effect even from both sources, with the driver getting no direct impact from the gamma rays. This is contrasted to continuous radiologic sources of 0.75 curies. Moreover, there is no need for a high-dose radiologic extended source that reduces imaging resolution to 3"×3" and requires complex mechanical shuttering between multiple sources, both for cargo irradiation and to avoid the driver getting a dose. Additionally, the subject system does not require unsafe radiological inventory on site.

In summary, a safe, reliable and rapid system for the detection of nuclear materials within containers includes the use of pulsed high-intensity gamma rays that can penetrate a container and its contents and can be detected outside the container to provide a display in which high-Z material, including lead, uranium, plutonium and other nuclear substances that absorb gamma rays are detected as black regions on the display. In one embodiment, orthogonal pulsed gamma ray beams illuminate the container from two different directions to provide three-dimensional slices from which the existence and location of nuclear threat materials can be ascertained in as little as four seconds for a 40-foot container.

BRIEF DESCRIPTION OF THE DRAWINGS

These and other features of the subject invention will be better understood in connection with the Detailed Description, in conjunction with the Drawings, of which:

FIG. 6 is a diagrammatic illustration of the utilization of orthogonally-oriented pulsed gamma ray sources for illuminating a container within a drive-through portal in which a three-dimensional scan results in the detection of high-Z materials of less than 10 centimeters within the cargo of a container;

FIG. 7 is a diagrammatic illustration of the display of a high-Z material within the container of FIG. 6, illustrating the result of a 10-centimeter threat in a field of 250 cm by 600 cm;

FIG. 8 is an enlarged view of the image of FIG. 7 illustrating the 10-cm threat as it would appear in an image field of 30 cm by 30 cm;

DETAILED DESCRIPTION

Figure 1:
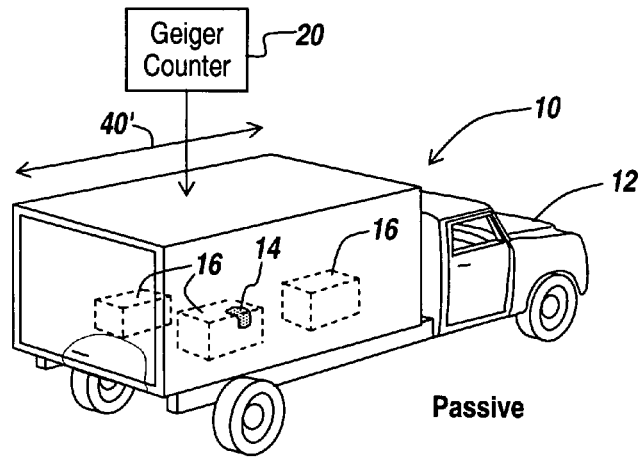
FIG. 1 is a diagrammatic illustration of a prior art passive scanning system utilizing a Geiger counter adjacent a container to detect the presence of nuclear material.

Referring now to FIG. 1, a container 10, which may be 40 feet in length, is located on a truck 12 that transports the container through a port facility.

In order to find out whether or not there is a threat 14 within cargo 16 in container 10, a Geiger counter 20 is utilized to passively detect radiation from threat 14 as it exits the container.

As mentioned hereinbefore, the problem with passive systems is that either lead that packages a threat or water itself, for instance in frozen food, can completely mask the radiation from threat 14.

Figure 2:
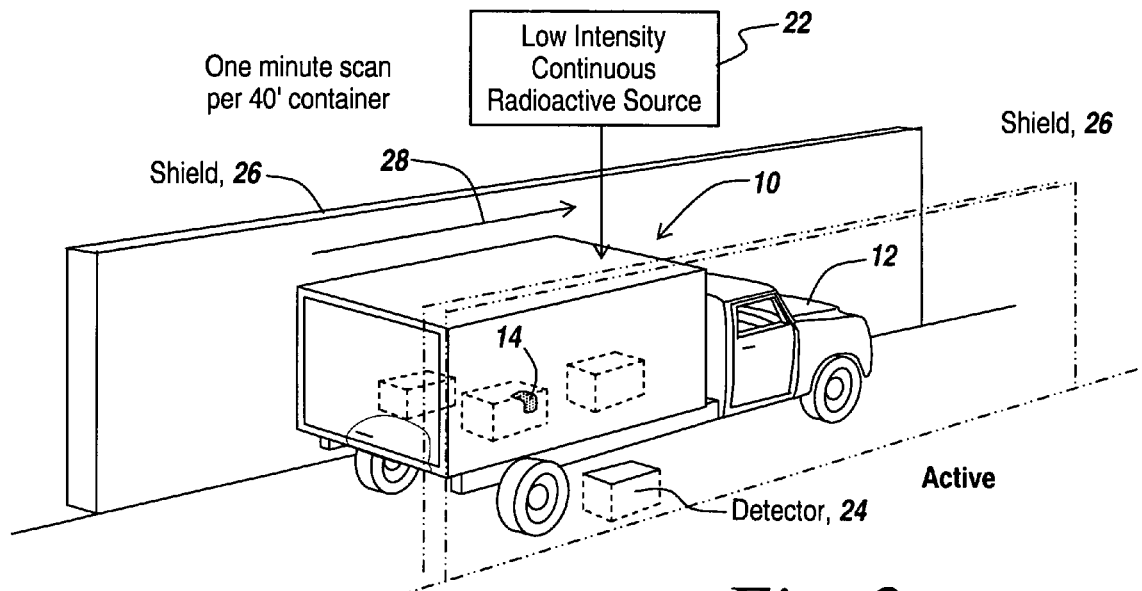
FIG. 2 is a diagrammatic illustration of a prior art low-intensity continuous radioactive source scanning system in which a 40-foot container can take more than one minute to scan.

Referring to FIG. 2, in another prior art system, in an active system, threat 14 is detected through the use of a low-intensity continuous radioactive source 22 that detects the attenuation of radiation from the source through the container to a detector 24. It is noted that in the case of utilizing radioactive sources there is a significant health hazard in addition to the inability to detect the low-intensity continuous radiation from the radioactive source. Note that shielding 26 is oftentimes required to surround the scanned area containing the truck and container.

Because of the low intensity of the radiologic source, the speed of the truck in the direction as illustrated at 28 is reduced to a speed that would enable the collection of the gamma rays at detector 24. This oftentimes requires the truck to be stationary. The result of such a system is not only the hazard involved in continuous radioactive sources adjacent individuals, it is also the fact that taking one minute or more to scan a container results in the inability to scan all of the containers, for instance, as they are being offloaded from a ship.

Figure 3:
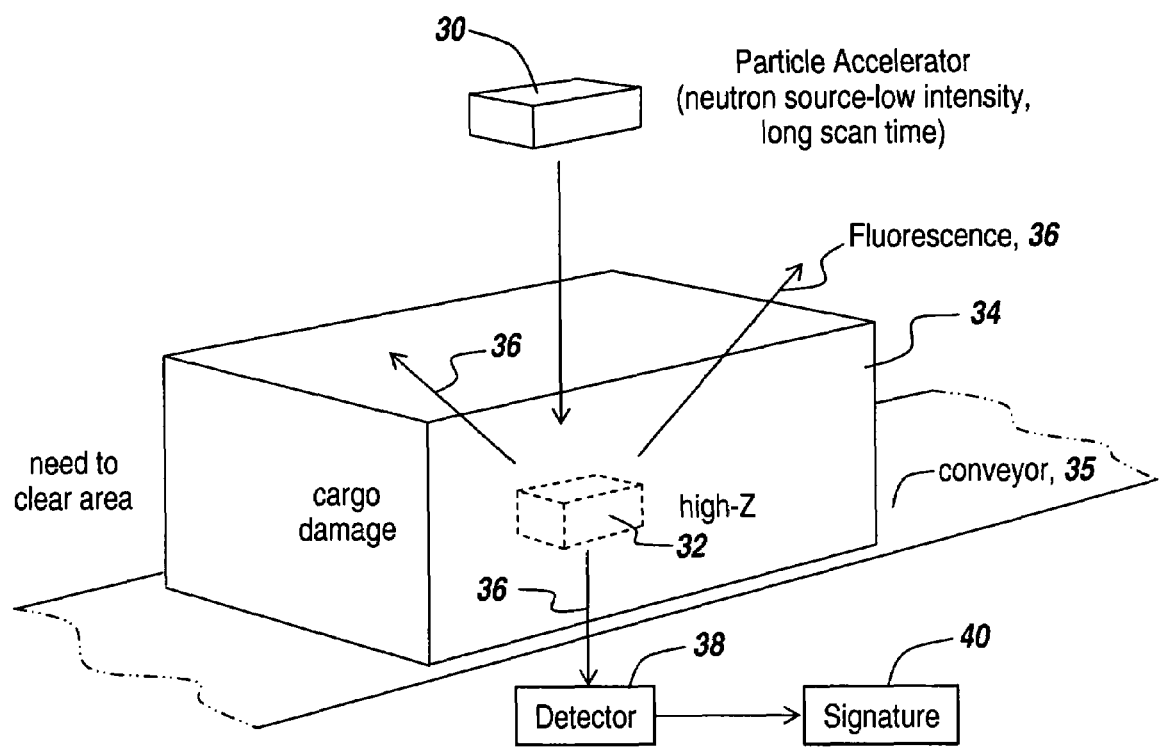
FIG. 3 is a diagrammatic illustration of prior art scanning of a cargo container, for instance on a conveyor utilizing a particle accelerator low-intensity neutron source with a fluorescence detector for obtaining the signature of the fluorescing radiation.

Referring to FIG. 3, in an alternative scanning procedure, a particle accelerator 30 that emits low-intensity neutrons used to detect the presence of a high-Z material 32 within a container 34 by bombarding the high-Z material with neutrons. The result is that the bombarded nuclei fluoresce and provide fluorescence 36, a portion of which is detected by detector 38, from which a signature 40 can be derived.

As mentioned hereinbefore, not only is there a need to clear the area due to the utilization of neutron beams, there can be cargo damage, injury to stowaways within a container and can take an exceedingly long time due to the low intensity of the neutrons from the particle accelerator.

Figure 4:
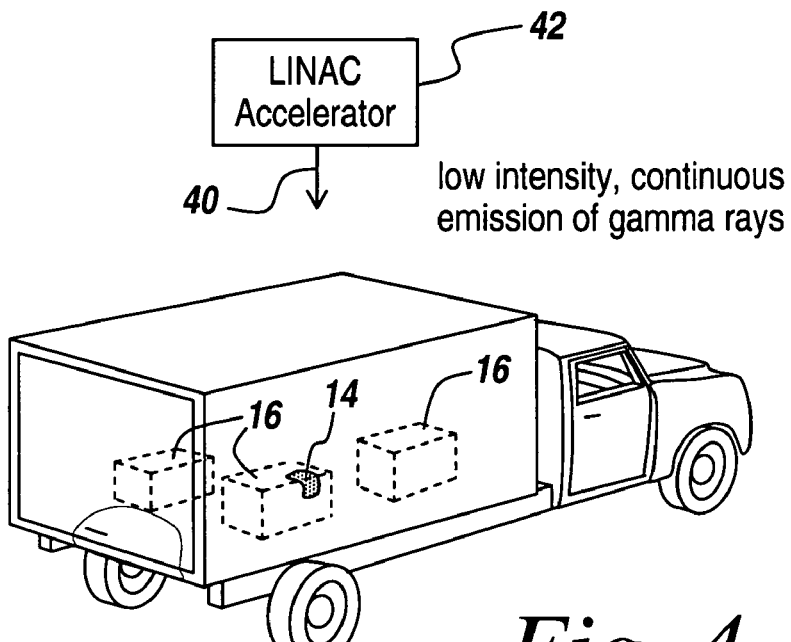
FIG. 4 is a diagrammatic illustration of a prior art low-intensity continuous emission gamma ray scanner utilizing a LINAC accelerator.

Referring now to FIG. 4, in a still further prior art embodiment, container 10 having a threat amongst cargo 16 is irradiated with low-intensity continuous gamma rays 40 from a LINAC accelerator 42.

The problem with such a system as described above is the low intensity of the source, the continuous nature of the emissions and the inability to accurately detect the presence of a threat.

Figure 5:
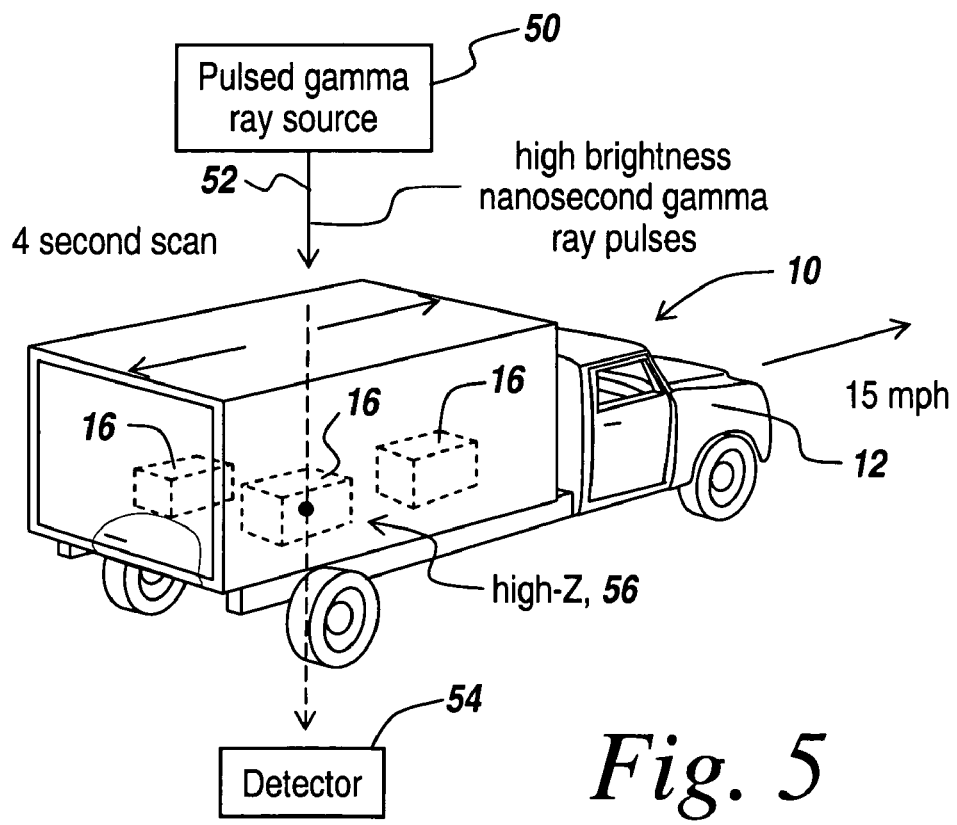
FIG. 5 is a diagrammatic illustration of a high brightness picosecond pulsed gamma ray source for inspecting cargo in a 40-foot container, with a scan requiring only four seconds.

Referring now to FIG. 5, in the subject invention a pulsed gamma ray source 50 is used that provides high brightness, picosecond gamma ray pulses projected as seen along arrow 52 through container 10, where they pass through the container and cargo 16 and are detected by a detector array 54.

The presence of a high-Z material 56, be it lead or some higher-weight element such as uranium or plutonium, is detected by detector 54 due to the absorption of the gamma rays by the high-Z material.

In this particular case, with the 1-3 MeV energies of the gamma rays, truck 12 can be driven through a detector kiosk or station at 15 miles per hour, meaning that the entire 40-foot container can be scanned in four seconds as opposed to the aforementioned multiple-minute scan times, assuming two pulses from each of the two sources.

The result of being able to scan in a four-second time interval means that 100% of the cargo from a ship can be scanned as opposed to sampling the cargo due to monetary constraints.

Referring to FIG. 6, in one embodiment a portal 60 is provided with orthogonally-oriented pulsed gamma ray sources 62 and 64. These gamma ray sources provide beams 66 and 68 respectively, which pass through container 70 and its contents, whereupon detector arrays 72 and 74 detect those portions of the beams that exit the far side of the container.

In one embodiment the distance of the pulsed gamma ray source from the top of container 70 is 11.47 feet, as is the spacing of the near side of the container from pulsed gamma ray source 64. The detector arrays are 8.5 feet long in one embodiment.

The outputs of the detectors are supplied to a processor 76 coupled to a display 78 that displays the presence of a high-Z material as a darkened portion 80 on the display.

The pulsed gamma ray sources are synchronized such that slices of the container are taken as the container moves through the portal. The time of the scans is inputted as illustrated by arrow 82 such that what is displayed on display 78 is a particular slice of the container, the location of which is determined by the slice number.

Referring to FIG. 7, for a twenty-foot equivalents units, TEU, 40-foot container, assuming a 10-cm threat in a container loaded to maximum weight with 20-cm water spheres approximating that of bottled water or frozen fish, the result is a darkened area 90 at a position approximately 280 cm along the X direction and approximately 130 cm along the Y direction.

As illustrated in FIG. 8, when this is enlarged by zooming in, one can easily see the 10-cm threat 90 on a scale that would indicate its ready visibility.

Figure 9:
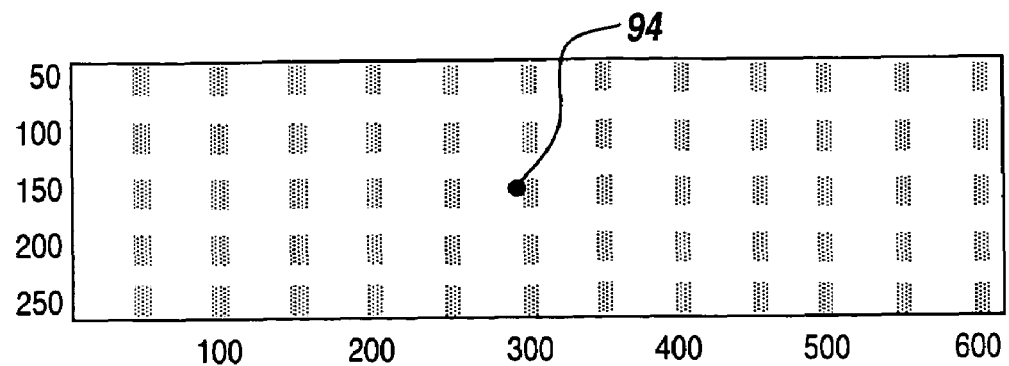
FIG. 9 is a diagrammatic illustration of the portrayal of a 10-cm threat in a container load in which the 10-cm threat replaces one of 226 engine blocks in a field of 250 cm by 600 cm; and, FIG. 10 is an enlargement of the image of FIG. 9, illustrating the ½-inch resolution of the subject system.

On the other hand and referring now to FIG. 9, for a TEU container with a 10-cm threat replacing one of 226 engine blocks, a small indication or dark area 94 is illustrated amongst the returns from the cargo being irradiated by the subject source.

Figure 10:
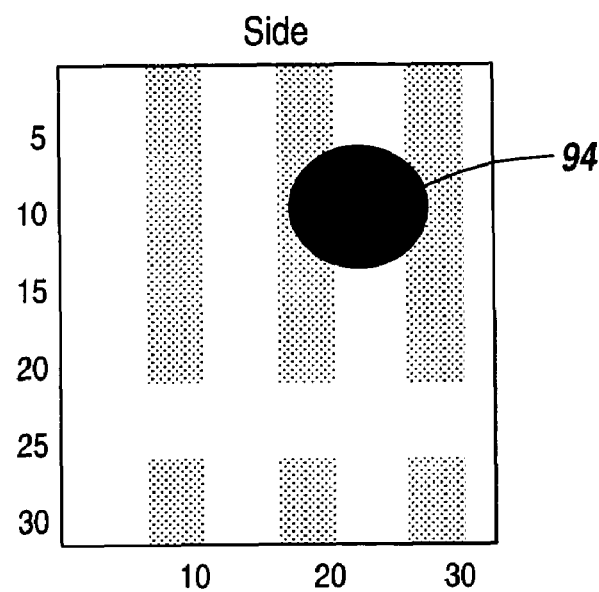

Referring to FIG. 10, in an enlarged view, threat 94 is clearly visible amongst the shadow lines relating to the type of scanning involved.

In any event, it is possible with the subject invention to scan containers at a rapid rate safely and accurately such that 100% of the containers of a cargo ship can be inspected, rather than the current sampling procedures.

Moreover, the radiation from the pulsed gamma source, since it is pulsed, is no more radiation than one would expect from a dental X-ray and as such is relatively safe to the individuals in the port or at the portal at which the container is scanned.

Moreover, since the source is controllable, it can be turned off while the driver is positioning the container underneath the source.

Note, while the subject invention is described in terms of cargo containers, any type of container is within the scope of this invention.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for detecting high-Z nuclear materials or high-Z nuclear material containers inside a cargo container in a safe, reliable and rapid manner to permit scanning large numbers of containers, comprising the steps of:
   generating a pulsed high-density beam of gamma rays having a duration of a picosecond or shorter and capable of penetrating a container having first and second opposed sides;
   directing the beam at the first side of the container; and,
   detecting the beam at the second side of the container, whereby high-Z material inside the container absorbs the beam of gamma rays so that a diminution of detected gamma rays at the second opposed side indicates the presence of high-Z material and thus a potential nuclear material threat.

2. The method of claim 1, wherein the step of generating a pulsed high-density beam of gamma rays includes the step of providing picosecond or shorter gamma ray pulses.

3. The method of claim 1, wherein the step of generating a pulsed high-density beam of gamma rays includes the step of providing two pulsed gamma ray sources oriented to provide orthogonal gamma ray beams through the container, and wherein the detecting step includes detecting the two beams after they exit the container, and further including the step of utilizing the detection of the two beams to generate a three-dimensional image, whereby the existence and position of high-Z material are ascertained.

4. The method of claim 3, wherein the pulsed gamma ray sources provide two pulses per slice, whereby a 40-foot container is scanned in less than four seconds.

5. The method of claim 1, and further including the step of providing a portal for a facility having a source of the pulsed high-density beam of gamma rays at one position on the portal and having an array of detectors at a diametrically opposite position of the portal and driving the container through the portal at a normal speed associated with moving the container about the facility.

6. The method of claim 5 wherein the facility is a port and wherein the normal speed is 15 miles per hour, whereby port activity is not impacted by the scanning of containers utilizing the pulsed high-density beam of gamma rays.

7. The method of claim 1, wherein the intensity of the gamma ray beam results in a dose within the cargo container less than $\frac{1}{20}$th of that associated with a dental X-ray.

8. The method of claim 1, wherein the radiation level in the container is less than 0.1 mrem.

9. The method of claim 1, wherein indirect dosing of individuals adjacent the gamma ray beam but not in its direct path due to scattering is no more than 0.001 mrem.

10. The method of claim 1, wherein the detection step includes the use of bulk CdZnTe detectors.

11. The method of claim 10, wherein the bulk CdZnTe detectors are grown utilizing the horizontal Bridgeman technique.

12. A method for rapidly and safely detecting the presence of nuclear threat material in cargo offloaded at a port in containers, comprising the steps of:
    irradiating a container with non-continuous pulsed gamma rays, the pulses of the gamma rays having pulse lengths in the picosecond or smaller region, whereby gamma ray intensities are high and safety hazards are low; and,
    detecting the presence of the nuclear threat material from the irradiation that exits the container, whereby the use of pulsed gamma rays increases the intensity of the gamma rays to permit robust detection while not presenting a safety hazard.

13. The method of claim 12, wherein the detecting step for a 40-foot container takes no more than four seconds, whereby continuous low-level gamma source systems that require minutes for a detection are avoided.

14. The method of claim 12, and further including the step of irradiating the container from two orthogonal directions with pulsed gamma rays and wherein the detecting step includes providing a three-dimensional display of the radiation detected that exits the container to provide darkened areas on the display to indicate the presence and location of the nuclear threat material.

15. The method of claim 13, wherein the presence of nuclear threat material is indicated by the absorption of the pulsed gamma rays by high-Z material.

16. The method of claim 15, wherein the nuclear threat material is contained in a high-Z material that absorbs gamma rays.

17. A system for rapidly detecting nuclear threat materials in a container, comprising:
    a portal;
    a pulsed source of gamma rays located at the portal, the gamma ray pulses having a duration of a picosecond or less;
    an array of detectors for detecting gamma rays at a position at the portal opposite the position of said source; and,
    a display coupled to said detectors for displaying the existence and location of said nuclear threat material in said container, whereby when said container is moved through said portal, said nuclear threat material is rapidly detected.

18. The system of claim 17, wherein said portal is at a facility and further including a vehicle for moving said container through said portal at a speed sufficiently high so as not to impact the traffic flow.

19. The system of claim 18, wherein said speed is the normal speed of vehicles at said port is 15 miles per hour.

* * * * *